United States Patent [19]

Burk

[11] 4,241,080
[45] Dec. 23, 1980

[54] STABILIZED AQUEOUS ANTIMICROBIAL COMPOSITION

[75] Inventor: George A. Burk, Bay City, Mich.

[73] Assignee: The Dow Chemical Company, Midland, Mich.

[21] Appl. No.: 43,064

[22] Filed: May 29, 1979

Related U.S. Application Data

[63] Continuation of Ser. No. 860,498, Dec. 14, 1977, abandoned.

[51] Int. Cl.$^3$ .................... A01N 37/18; A01N 37/34; A01N 43/36; A01N 43/40
[52] U.S. Cl. .................................. 424/304; 424/244; 424/267; 424/274; 424/320; 424/324
[58] Field of Search ............... 424/304, 320, 324, 244, 424/267, 274

[56] References Cited

U.S. PATENT DOCUMENTS

| 3,689,660 | 9/1972 | Burk et al. | 424/304 |
| 3,751,444 | 8/1973 | Solem et al. | 260/465.4 |
| 3,770,798 | 11/1973 | Norton | 260/465.5 R |
| 4,022,605 | 5/1977 | Konya et al. | 424/304 |

OTHER PUBLICATIONS

Chemical Abstracts, vol. 82 (1975), p. 139619v.

*Primary Examiner*—Allen J. Robinson
*Attorney, Agent, or Firm*—James B. Guffey

[57] ABSTRACT

Aqueous antimicrobial compositions which comprise a halogenated amide antimicrobial, such as 2,2-dibromonitrilopropionamide, a water miscible organic solvent such as a straight chain polyalkylene glycol (e.g., polyethylene glycol 200) or an ether thereof (e.g., a mono- or di-lower alkyl and/or phenyl ether) and water are stabilized against decomposition of the halogenated amide antimicrobial by the addition of an acid or anhydride stabilizer such as acetic acid, glycolic acid, boric acid, ethylenediaminetetraacetic acid, succinic anhydride, etc. The compositions, so stabilized, exhibit reduced rates of decomposition of the halogenated amide antimicrobial relative to the corresponding non-stabilized aqueous compositions.

20 Claims, No Drawings

STABILIZED AQUEOUS ANTIMICROBIAL COMPOSITION

This application is a continuation of my copending patent application Ser. No. 860,498, filed Dec. 14, 1977 now abandoned.

BACKGROUND OF THE INVENTION

This invention relates to stabilized aqueous antimicrobial compositions which comprise a halogenated amide as the active (i.e., antimicrobial) ingredient and to processes for their preparation.

Halogenated amides such as 2,2-dibromonitrilopropionamide are useful as antimicrobials in various applications. See, for example, Nolan et al., U.S. Pat. No. 2,419,888; Schmidt et al., U.S. Pat. No. 3,493,658; and CIBA S.A. Belgian Pat. No. 668,336. Certain halogenated amides are useful in the finishing of textiles, as taught by Chance et al., U.S. Pat. Nos. 3,350,164 and 3,403,174. Others are useful as slimicides in aqueous systems such as paper pulp and cooling towers and as sterilizing agents for drycleaning fluids. See, for example, Wolf, U.S. Pat. No. 3,647,610; Wolf, U.S. Pat. No. 3,649,166; Wolf et al., "2,2-Dibromo-3-Nitrilopropionamide, A Compound with Slimicidal Activity", Applied Microbiology, Vol. 24, No. 4, pp. 581-584 (1972); and Moyle et al., U.S. Pat. No. 3,928,575.

In the storage, shipment and use of such antimicrobial agents, it is often desirable to employ the antimicrobial agent in the form of a liquid concentrate composition wherein the halogenated amide antimicrobial is dissolved in a mixture of an organic solvent and water. However, the presence of water in such compositions often accelerate decomposition of the halogenated amide antimicrobial. See, for example, U.S. Pat. No. 3,689,660 and "Rates and Products of Decomposition of 2,2-Dibromo-3-Nitrilopropionamide", Exner et al., J. Agr. Food Chem., Vol. 21, No. 5, pp. 838-842 (1973). Accordingly, in order to obtain adequate stability for many purposes, it has heretofore been necessary to resort to essentially anhydrous liquid concentrate compositions and it has therefore been necessary to essentially exclude water from the ingredients used in the preparation thereof.

Consequently, it is desirable to provide a means of reducing the adverse impact of water upon the aforementioned liquid concentrate compositions and to thereby provide (a) aqueous halogenated amide antimicrobial compositions having improved stability and (b) simplified, economical processes for the preparation of stable liquid concentrate compositions.

SUMMARY OF THE INVENTION

It has now been found that the rate of decomposition of the halogenated amide antimicrobial in the aforementioned aqueous liquid concentrate compositions is substantially reduced by the addition of certain acid or anhydride stabilizers. Thus, in one aspect the instant invention is a stabilized aqueous antimicrobial composition which comprises (1) a water miscible organic solvent; (2) water; (3) a halogenated amide antimicrobial; and (4) a stabilizing amount of an acid or anhydride stabilizer selected from the group consisting of acetic acid, ethylenediaminetetraacetic acid, succinic acid, succinic anhydride, glycolic acid, boric acid, salicylic acid and citric acid. Typically, such composition has a pH of from about 2 to about 5 (preferably from about 3 to about 4).

In another aspect the instant invention is a process for preparing an aqueous halogenated amide antimicrobial composition wherein the aqueous component of such composition comprises the aqueous reaction medium in which the halogenated amide antimicrobial was prepared. Such process comprises the steps of:

(a) preparing the halogenated amide antimicrobial by the acid catalyzed reaction of a non-halogenated amide with halogen in aqueous solution;

(b) dissolving the resulting aqueous reaction mixture in a water miscible organic solvent; and (c) adding to the reaction mixture, or to the water miscible organic solvent solution thereof, a stabilizing amount of an acid or anhydride stabilizer selected from the group consisting of acetic acid, ethylenediaminetetraacetic acid, succinic acid, succinic anhydride, glycolic acid, boric acid, salicylic acid and citric acid.

Typically, the aforementioned process also involves a pH adjustment step such that the composition resulting from such process has a pH of from about 2 to about 5, preferably from about 3 to about 4.

As used herein, the term "water miscible" means that the organic solvent is soluble in water (i.e., mixes or blends uniformly with water) at least to the degree required to achieve the desired solvent to water ratio in the aqueous composition and preferably such solvent is soluble in water in all proportions.

The terms "antimicrobial compound" and "halogenated amide antimicrobial" are used interchangeably herein and refer to halogenated amides which function as biocides (i.e., compounds which inhibit the growth of, or kills, microorganisms such as bacteria, molds, slimes, fungi, etc.).

The term "stabilizing amount" as employed herein refers to an amount of an acid or anhydride stabilizer sufficient to measurably reduce the decomposition rate of the halogenated amide antimicrobial in the aqueous antimicrobial composition. The aforementioned reduction in the decomposition rate of the halogenated amide antimicrobial is, of course, relative to the decomposition rate encountered with a corresponding aqueous antimicrobial composition in the absence of the acid or anhydride stabilizer under the same test conditions. Such reduction is deemed to be "measurable" if it is detectible (and reproducible) by the iodometric test method which is described hereinafter in conjunction with the working examples.

The aqueous antimicrobial compositions of the invention are useful as slimicides in aqueous systems such as paper pulping processes and cooling towers and as sterilizing agents for drycleaning fluids. Such compositions exhibit improved stability toward decomposition of the halogenated amide antimicrobial for extended periods under a wide variety of storage, packaging and handling conditions. They are easily handled and can be employed in the above applications pursuant to conventional techniques such as those described in U.S. Pat. No. 3,689,660.

The indicated process for preparing the aqueous antimicrobial composition is advantageous in that suitably stable compositions can be prepared without separation of the halogenated amide antimicrobial from the aqueous medium in which it was prepared.

DETAILED DESCRIPTION OF THE INVENTION

Halogenated amide antimicrobials employed in the practice of this invention are alpha-haloamides; that is, compounds which contain an amide functionality (i.e., a moiety of the formula —C(O)—N<) and which have at least one halogen atom on a carbon atom located adjacent to (i.e., in the alpha position relative to) the carbonyl group (i.e., the —C(O)— group) of such amide functionality. Advantageously, such halogenated amide antimicrobials are halogenated nitrilopropionamides or halogenated malonic diamides having the formula:

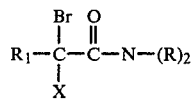

wherein:

X is hydrogen, halogen or a cyano radical, i.e., —C≡N, (preferably hydrogen, chlorine or bromine);

each R group is independently hydrogen, a monovalent "saturated hydrocarbon radical" or an inertly substituted monovalent "saturated hydrocarbon radical" or the two R groups are, jointly, a divalent "saturated hydrocarbon radical", or an inertly substituted divalent "saturated hydrocarbon radical", which, taken with the adjacent nitrogen atom, forms a heterocyclic ring having from 4 to about 10 ring members; and $R_1$ is a cyano radical (i.e., —C≡N) or an amido radical having the formula:

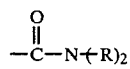

wherein R is as hereinbefore defined. (Preferably $R_1$ is a cyano radical).

As used herein, the term "saturated hydrocarbon radical" refers to a hydrocarbon radical which is free of aliphatic carbon to carbon unsaturation. Thus, such term includes radicals such as alkyl, cycloalkyl, aryl, alkylaryl, arylalkyl, cycloalkylaryl, etc., and excludes radicals such as alkenyl, cycloalkenyl, alkynyl and the like.

As used herein, the term "inertly substituted saturated hydrocarbon radical" refers to a "saturated hydrocarbon radical" having one or more chain linkage or substituent which is "inert" in the sense that such chain linkage or substituent does not readily react with the ingredients of the aqueous antimicrobial composition. Suitable inertly substituted saturated hydrocarbon radicals thus include, for example, haloalkyl, haloaryl, halocycloalkyl, aminoalkyl, aminoaryl, aminocycloalkyl, hydroxyalkyl, hydroxyaryl, hydroxycycloalkyl, cyanoalkyl, cyanoaryl, cyanocycloalkyl, and the like.

The aforementioned halogenated amide antimicrobials of the formula I thus include brominated nitrilopropionamides (i.e., compounds of the formula I wherein $R_1$ is a cyano radical), such as 2-bromo-3-nitrilopropionamide, 2bromo-2,3-dinitrilopropionamide, 2,2-dibromo-3-nitrilopropionamide, N-(n-butyl)-2-bromo-3-nitrilopropionamide; N,N-dimethyl-2,2-dibromo-3-nitrilopropionamide, 2-chloro-2-bromo-3-nitrilopropionamide, N-(n-propyl)-2-iodo-2-bromo-3-nitrilopropionamide, N-methyl-N-ethyl-2-fluoro-2-bromo-3-nitrilopropionamide, N-phenyl-2-cyano-2-bromo-3-nitrilopropionamide, N-cyclohexyl-2,2-dibromo-3-nitrilopropionamide, N-benzyl-2-bromo-3-nitrilopropionamide, N-(2,2-dibromo-3-nitrilopropionoyl)-piperidine, and the like.

The aforementioned halogenated amide antimicrobials of the formula I also include mono- and di-bromomalonic diamides (i.e., compounds of the formula I wherein $R_1$ is an amido radical as hereinbefore described), such as 2-bromomalonic diamide, 2,2-dibromomalonic diamide, N-methyl-N'-ethyl-2-chloro-2-bromomalonic diamide, N-phenyl-2-iodo-2-bromomalonic diamide, and the like.

Among the aforementioned halogenated amide antimicrobials, those wherein, in the formula I, $R_1$ is a cyano radical, X is hydrogen, chlorine or bromine and each R is independently hydrogen, lower alkyl (i.e., an alkyl group of from 1 to about 6 carbon atoms) or phenyl are preferred, especially those of the formula I wherein each R independently is hydrogen or methyl and X is hydrogen or bromine. Such halogenated amide antimicrobials include 2-bromo-3-nitrilopropionamide, 2,2-dibromo-3-nitrilopropionamide, N-methyl-2-bromo-3-nitrilopropionamide, N-phenyl-2-bromo-2-chloro-3-nitrilopropionamide, N-methyl-2,2-dibromo-3-nitrilo-propionamide, N,N-dimethyl-2-bromo-3-nitrilopropionamide, N,N-diethyl-2,2-dibromo-3-nitrilopropionamide, and N,N-dimethyl-2,2-dibromo-3-nitrilopropionamide.

Also of particular interest are the dibrominated nitrilopropionamides (i.e., the halogenated amide antimicrobials of the formula I wherein X is bromine and $R_1$ is cyano) wherein each R independently is hydrogen, lower alkyl (i.e., containing from 1 to about 6 carbon atoms) or phenyl. Such compounds include 2,2-dibromo-3-nitrilopropionamide, N-(n-butyl)-2,2-dibromo-3-nitrilopropionamide, N,N-dimethyl-2,2-dibromo-3-nitrilopropionamide, N-phenyl-N-methyl-2,2-dibromo-3-nitrilopropionamide and the like; especially 2,2-dibromo-3-nitrilopropionamide.

The aqueous antimicrobial compositions of the invention normally contain from about 1 to about 25 percent by weight of the hereinbefore described halogenated amide antimicrobial based upon the total weight of the composition. However, the decomposition of the halogenated amide antimicrobials has been observed to be more pronounced when the aqueous compositions contain less than about 20 percent by weight of the antimicrobial on a total weight basis. Thus, stabilized aqueous antimicrobial compositions which, by virtue of the relatively more pronounced benefits of stabilization, are of particular interest comprise from about 1 to about 15, preferably from about 1 to about 10, most preferably from about 1 to about 5, weight percent of the total composition.

In the practice of this invention, the aforementioned halogenated amide antimicrobial is dissolved in a mixture of water and a water miscible organic solvent. Suitable organic solvents include any water miscible organic solvent in which the halogenated amide antimicrobial is at least partially soluble. Preferably the organic solvent is one in which the halogenated amide antimicrobial is soluble at normal room temperature (i.e., from about 20° to about 25° C.) to the extent of at least about 5 parts by weight of the antimicrobial in about 95 parts by weight of the solvent. The most preferred water miscible organic solvents are those in which the antimicrobial is soluble to the extent of at least about 10 (especially at least about 20) parts by weight of the antimicrobial in about 80 parts by weight of the solvent at normal room temperatures (i.e., from about 20° to about 25° C.).

Advantageously, the organic solvent is a polyalkylene glycol or an ether thereof, especially a normally liquid straight chain polyalkylene glycol or a mono- or di-saturated hydrocarbyl ether thereof wherein the term "saturated hydrocarbyl" refers to a monovalent saturated hydrocarbon radical as hereinbefore defined. Generally, such polyalkylene glycols and polyalkylene glycol ethers have a weight average molecular weight (Mw) of from about 75 to about 1000. Such average molecular weights are hereinafter designated for the particular glycols involved by placing a numeral representing the weight average molecular weight after the glycol name.

Of particular interest in the practice of the invention are the polyalkylene glycols of the ethylene, trimethylene or tetramethylene series and the mono- and di-lower (e.g., containing from 1 to about 6 carbon atoms) saturated hydrocarbyl ethers thereof. Examples of such particularly advantageous solvents include polyethylene glycols, trimethylene glycols, tetramethylene glycols and the mono- and di-lower saturated hydrocarbyl (e.g., lower, i.e., $C_1$ to about $C_6$, alkyl and phenyl) ethers of such glycols. Examples of such glycols and ethers include 1,4-butanediol, triethylene glycol, polyethylene glycol 200, tetraethylene glycol, polyethylene glycol 400, diethylene glycol dimethyl ether, diethylene glycol phenyl ether, diethylene glycol ether phenyl ether, polytrimethylene glycol 200, diethylene glycol, triethylene glycol methyl ether and polyethylene glycol 600.

Preferably, the polyalkylene glycol or ether ingredient is a polyethylene glycol, or a mixture of polyethylene glycols, having Mw of from about 175 to about 250. Most preferably the polyalkylene glycol ingredient is polyethylene glycol 200.

The amount of the aforementioned water miscible organic solvent employed in the practice of the invention is not particularly critical. Advantageously, however, a sufficient amount is employed to prevent precipitation of the halogenated amide antimicrobial during shipping, storage and use of the aqueous antimicrobial composition. The amount of the organic solvent desirably employed will thus depend upon such factors as the solubility of the halogenated amide antimicrobial in the organic solvent, the desired concentration of the halogenated amide antimicrobial in the composition, and the like. However, as a general rule the organic solvent constitutes from about 5 to about 90, preferably from about 10 to about 80, more preferably from about 25 to about 75, most preferably from about 35 to about 70, percent by weight of the total antimicrobial composition.

As has been noted, any of the aforementioned water miscible organic solvents can be suitably employed in the practice of this invention to dissolve the aforementioned halogenated amide antimicrobial. However, it has been found (and such finding constitutes the subject matter of a commonly owned application by George A. Burk, Charles A. Wilson and Charles E. Reineke filed even date herewith) that the aforementioned problem of halogenated amide decomposition under aqueous conditions is substantially more pronounced in the presence of salts or organic acids and/or glycols having a molecular weight of less than about 70 grams per mole; both of which, for example, are potentially common minor impurities in many commercially available unpurified polyalkylene glycols and ethers thereof. Thus, the benefits attributable to the herein disclosed stabilizers are relatively more pronounced in those stabilized aqueous antimicrobial compositions which employ organic solvents containing the aforementioned impurities or which contain such impurities from some other source.

The amount of water contained by the aqueous antimicrobial composition of the invention is likewise not particularly critical to the practice of the invention. However, as a general rule the compositions of the invention employ water in an amount of from about 5 to about 90, preferably from about 10 to about 85, more preferably from about 15 to about 70, most preferably from about 20 to about 60 weight percent based upon the weight of the total antimicrobial composition.

The acid or anhydride stabilizer employed in the practice of this invention is selected from the group consisting of acetic acid, ethylenediaminetetraacetic acid, succinic acid, succinic anhydride, glycolic acid, boric acid, salicylic acid and citric acid.

Preferably the acid or anhydride stabilizer is selected from the group consisting of acetic acid, ethylenediaminetetraacetic acid, succinic acid, cuccinic anhydride, glycolic acid and boric acid.

More preferably the acid or anhydride stabilizer is selected from the group consisting of acetic acid, ethylenediaminetetraacetic acid, succinic acid, succinic anhydride and glycolic acid.

Most preferably the acid or anhydride stabilizer is selected from the group consisting of acetic acid; ethylenediaminetetraacetic acid; succinic acid and succinic anhydride; and acetic acid is especially desirable because of its low cost and ready availability.

The hereinbefore described acid or anhydride stabilizer is employed in the practice of the invention in a "stabilizing amount", which term is defined hereinbefore. Advantageously, such stabilizer is employed in an amount sufficient to reduce by at least about 20 percent (preferably by at least about 30 percent and most preferably by at least about 40 percent) the amount of antimicrobial compound which decomposes during about 15 days (preferably about 30 days) of storage at 50° C. Such decomposition reduction is, of course, relative to that which occurs under the same conditions in the absence of the aforementioned stabilizer. In quantitative terms, the amount of stabilizer needed to achieve the desired degree of stabilization can vary depending upon the remainder of the composition (i.e., the identity and concentration of the other ingredients in the particular composition involved) and upon the particular stabilizer employed. However, as a general rule the stabilizer constitutes between about 0.05 and about 10, preferably between about 0.1 and about 5, most preferably between about 0.5 and about 2, percent by weight of the total composition.

In addition to the hereinbefore defined ingredients, the aqueous antimicrobial composition of the invention can optionally contain other ingredients. Such optional ingredients can be inert in the sense that they neither inhibit nor accelerate decomposition of the antimicrobial compound. Alternatively, such optional ingredients can themselves be stabilizers for the halogenated amide antimicrobial. Thus, for example, the stabilized aqueous antimicrobial composition of the invention can, in addition to the aforementioned acid or anhydride stabilizer, further comprise other compounds which are stabilizers in their own right as disclosed in commonly owned applications filed even date herewith. Such optional additional stabilizers thus include carbamoyl or sulfamoyl compounds (e.g., N-methyl urea, N,N-diethyl urea, biuret, sulfamide, oxamide, N,N-dimethylformamide, caprolactam, N-methyl-2-pyrrolidone, dimethylhydantoin, succinimide, etc.) as disclosed by George A. Burk and Charles E. Reineke; ethers (e.g., 1,4-dioxane, tetrahydrofuran, sym-trioxane, N-methyl morpholine, etc.) as disclosed by George A. Burk and Charles A. Wilson; aldehydes (e.g., formaldehyde, paraformaldehyde, N-formyl piperidine, vanillin, etc.) as disclosed by George A. Burk, Charles A. Wilson and Charles E. Reineke; quaternary salts (e.g., methyl triphenyl phosphonium bromide, n-$C_{12}$-$C_{18}$ alkyl dimethylbenzyl ammonium chloride, etc.) as disclosed by George A. Burk; and azine or nitrile compounds (e.g., cyanuric acid, 2-chloro-4,6-bis(ethylamino)-s-triazine, cyanoguanidine, succinonitrile, etc.) as disclosed by George A. Burk. The amount of such other stabilizer which is desirably employed varies depending upon a number of factors, such as the identity and amounts of the specific ingredients involved. However, as a general rule between about 0.1 and about 2, preferably between about 0.2 and about 1 percent by weight is employed based upon the total weight of the antimicrobial composition.

The order of combination of the hereinbefore described ingredients is not critical to the obtention of a decreased decomposition rate relative to that obtained with the corresponding non-stabilized composition. However, in order to avoid excessive amounts of decomposition prior to stabilization, it is generally desirable to avoid prolonged exposure of the antimicrobial compound to the water in the composition prior to addition of the stabilizer thereto. In addition, it is generally desirable, in order to retain optimum antimicrobial activity, to prepare, store, transport and handle the stabilized compositions of the invention at the lowest practicable temperature (normally ambient temperature). Similarly, it is desirable that the pH of the compositions of the invention be maintained at a value between about 2 and about 5 (preferably between about 3 and about 4) since the decomposition of the antimicrobial under aqueous conditions (both with and without stabilization) is typically minimized within such pH range.

As has been noted, the hereinbefore described stabilizers have been found to reduce the halogenated amide antimicrobial decomposition rate in a mixture of an organic solvent and water. A particularly beneficial result of such phenomenon is that suitably stable halogenated amide antimicrobial compositions can be prepared directly from a mixture of the antimicrobial and the aqueous reaction medium in which it was prepared. Specifically, separation of the halogenated amide antimicrobial from its aqueous reaction medium is conveniently eliminated by incorporating such reaction medium into the antimicrobial composition and by counteracting the adverse impact of the water thereby introduced into such composition by adding the aforementioned acid or anhydride stabilizer.

Thus, in one aspect this invention is a process for preparing the aforementioned stabilized aqueous antimicrobial compositions, which process comprises the steps of (a) preparing the halogenated amide antimicrobial by the acid catalyzed reaction of the corresponding non-halogenated amide with halogen in aqueous solution; (b) dissolving the resulting aqueous reaction mixture in the hereinbefore described water miscible organic solvent; and (c) adding to the reaction mixture, or to the water soluble organic solvent solution thereof, a stabilizing amount of one or more of the aforementioned acid or anhydride stabilizers. Typically, the aforementioned process also comprises an additional step in which the pH of the reaction mixture, the organic solvent solution, or the stabilized organic solvent solution is adjusted such that the pH of the antimicrobial composition is from about 2 to about 5, preferably from about 3 to about 4. Preferably, such pH adjustment step is performed following preparation of the halogenated amide and prior to dissolution of the reaction mixture in the organic solvent. In such instance, adjustment of the reaction mixture pH to a value of from about 5 to about 7 (preferably from about 5.5 to about 6.5) prior to dissolution typically provides the antimicrobial composition with a pH within the desired range following the dissolution step.

The particular reagent employed in the aforementioned pH adjustment step is not particularly critical. However, as a general rule, alkali metal or alkaline earth metal carbonates or bicarbonates (especially sodium carbonate) are advantageously employed.

The preparation of the halogenated amide antimicrobial (i.e., step (a) above) can be accomplished in any convenient conventional manner. Thus, for example, the halogenated amide antimicrobial can be prepared by the acid catalyzed reaction of the corresponding non-halogenated amide (e.g., cyanoacetamide, malonic diamide, and N-substituted derivatives thereof) with halogen (especially bromine) in aqueous solution, preferably at a temperature of less than about 40° C. and preferably at a hydrogen halide (which is a reaction by-product) concentration of less than about 20 weight percent on a total weight basis.

Preferably, however, the initial step of such process is performed pursuant to the improved procedure which is disclosed by U.S. Pat. No. 3,751,444. In such preferred process for preparing the halogenated amide antimicrobial, the improved aspect comprises introducing a water-soluble bromate into the aqueous reaction medium. Further details relating to the practice of such preferred initial step are found in U.S. Pat. No. 3,751,444; the disclosure of which is hereby incorporated by reference.

After the halogenated amide antimicrobial has been prepared, the resulting reaction mixture is dissolved in the hereinbefore described organic solvent. Such dissolution step is performed either before or after addition of the stabilizer and without isolation of the halogenated amide antimicrobial from the aqueous reaction medium. Any of the hereinbefore described water miscible organic solvents can be suitably employed in such dissolution step. However, as has been noted, the presence in such solvent of salts of an organic acid and/or glycols having a molecular weight of less than about 70 has been observed to deleteriously affect the stability of the halogenated amide antimicrobial. Accordingly, it is preferable (in order to obtain optimum stability in the resulting compositions of the instant process) to employ an organic solvent of the hereinbefore described type which is substantially free both of salts of organic acids and of glycols having molecular weights of less than about 70 grams per mole.

In the aforementioned process, it is generally desirable to avoid prolonged exposure of the halogenated amide antimicrobial to the aqueous reaction medium in the absence of the stabilizer in order to prevent excessive loss (i.e., decomposition) of the halogenated amide product prior to stabilization. In addition, the pH adjustment step is also desirably accomplished without prolonged delay since the decomposition rate of the halogenated amide antimicrobial is generally pH dependent and since such decomposition rate is typically minimized within the indicated pH range. In addition, since the rate of decomposition of the halogenated amide antimicrobial increases with increased temperature, it is preferable to conduct the aforementioned individual process steps (and to store, transport and handle the resulting aqueous antimicrobial compositions) at ambient temperature (e.g., from about 20° to about 25° C.) or less in order to avoid excessive decomposition of the antimicrobial during such operations.

Naturally, in the practice of the aforementioned process, other ingredients such as those described hereinbefore, can be added to the aqueous composition either during or after its preparation pursuant to such process.

The practice of the instant invention is further illustrated by the following examples. In such examples all weight percentages are on a total weight basis unless otherwise indicated. The polyethylene glycol 200 employed in such examples is a commercial grade mixture of polyethylene glycols having a weight average molecular weight of about 200 and commercially available as Polyglycol E-200 from the Dow Chemical Company.

EXAMPLE 1

Aqueous Solution of 2,2-Dibromo-3-Nitrilopropionamide in Polyethylene Glycol 200 Stabilized with Acetic Acid This example illustrates the stabilizing effect of acetic acid upon the decomposition of 2,2-dibromo-3-nitrilopropionamide (DBNPA) in an aqueous antimicrobial composition. Also illustrated is the increased rate of DBNPA decomposition in the presence of water in the absence of a stabilizer.

EXAMPLE 1

A 2.5 gram portion of 2,2-dibromo-3-nitrilopropionamide (DBNPA) is placed in a 2 oz amber bottle. To this is added a 23.5 gram portion of polyethylene glycol 200 (P.E.G. 200), a 23.5 gram portion of water, and a 0.5 gram portion of acetic acid.

Anhydrous Control

In a second 2 oz amber bottle is placed a 2.5 gram portion of DENPA and a 47.5 gram portion of P.E.G. 200.

Aqueous Control

In a third 2 oz amber bottle is placed a 2.5 gram portion of DENPA, a 23.75 gram portion of P.E.G. 200 and a 23.75 gram portion of water.

The contents of each of the three bottles are mixed at room temperature until the ingredients are dissolved. The dissolution is accompanied by a temperature rise of about 5° C. The bottles are closed with a polyethylene lined cap and placed in a constant temperature oven at 50° C. for accelerated decomposition testing. The samples are removed periodically and the extent of DBNPA decomposition is determined by iodometry. The results of such testing are summarized in Table I below.

In this example (and in the subsequent examples), the relative DBNPA content of the various antimicrobial compositions is determined by iodometry. In such test method, an excess of potassium iodide (KI) is added to the antimicrobial composition and the amount of elemental iodine which has been liberated from the KI (via oxidation of the KI by the DBNPA) is determined by titration with a standard solution of sodium thiosulfate. The amount of DBNPA present in the composition tested is then calculated on the basis of the amount of elemental iodine liberated thereby.

It should be noted that since certain of the intermediate decomposition products of DBNPA are also oxidizing agents, the indicated test method does not, strictly speaking, provide an exact measure of DBNPA content. However, such test method does provide a measure of the amount of DBNPA which has completely decomposed to the ultimate non-oxidizing species and thus provides a relative measure of the stability of the DBNPA compositions tested.

TABLE I

DBNPA CONTENT AS A FUNCTION OF STORAGE TIME AT 50° C.

| | DBNPA Remaining After the Indicated Storage Interval (weight percent) | | | | |
|---|---|---|---|---|---|
| | Initial | 5 Days | 13 Days | 20 Days | 27 Days | 32 Days |
| Anhydrous Control* | 5.0 | 4.92 | 4.80 | 4.71 | 4.50 | 4.31 |
| Aqueous Control* | 5.0 | 4.68 | 4.18 | 3.73 | 3.50 | 3.32 |
| Example 1 | 5.0 | 4.90 | 4.75 | 4.45 | 4.14 | 3.92 |
| Decomposition Prevented by Acetic Acid** | — | 69% | 70% | 57% | 43% | 36% |

*Not an example of the invention
**DBNPA of Example 1 minus DBNPA of Aqueous Control) ÷ (5.00 minus DBNPA of Aqueous Control); all times 100%

Comparison of the Anhydrous and Aqueous Controls illustrates the adverse effect of water upon the stability of DBNPA. For example, under aqueous conditions 34 percent of the DBNPA which was originally present decomposes during 32 days at 50° C., i.e., [(5.0−3.32)÷5.0]×100%. In contrast, the Anhydrous Control suffers a loss of only 14 percent of the DBNPA originally present over the same time period at 50° C., i.e., [(5.0−4.31)÷5.0]×100%. Similar differences in DBNPA decomposition between the Aqueous Control and the Anhydrous Control are reflected at the shorter test intervals.

The stabilizing effect of acetic acid is observed by comparing Example 1 with the Aqueous Control. Such comparison shows that the composition of the invention exhibits between 36 and 69 percent less DBNPA decomposition than does the corresponding non-stabilized aqueous composition; with the exact percentage figure depending upon the storage interval involved.

EXAMPLES 2–5

Stabilized Aqueous DBNPA—P.E.G. 200 Formulations

Solutions containing 5 weight percent DBNPA, 47 weight percent P.E.G. 200, 47 weight percent water and 1 weight percent of the indicated stabilizer are prepared, aged at 50° C., sampled and analyzed pursuant to the procedure of Example 1. The results are presented below and the corresponding data for the Aqueous Control of Example 1 and for Experiments A (formic acid) and B (oxalic acid) is also included for comparative purposes.

| | Acid Stabilizer | WEIGHT PERCENT DBNPA REMAINING AFTER THE INDICATED STORAGE TIME AT 50° C. | | | | | |
|---|---|---|---|---|---|---|---|
| | | 5 Days | 10 Days | 15 Days | 20 Days | 25 Days | 30 Days |
| Example 2 | Glycolic Acid | 4.78 | 4.56 | 4.35 | 4.12 | 3.87 | 3.60 |
| Example 3 | Boric Acid | 4.75 | 4.50 | 4.28 | 4.00 | 3.68 | 3.37 |
| Example 4 | Salicylic Acid | 4.88 | 4.75 | 4.63 | 3.73 | 2.93 | ≈2.00 |
| Example 5 | Citric Acid | 4.75 | 4.50 | 3.97 | 3.44 | 2.74 | 2.40 |
| Aqueous Control* | None | 4.68 | 4.37 | 4.04 | 3.73 | 3.56 | 3.39 |
| Experiment A* | Formic Acid | 4.58 | 4.17 | 3.77 | 3.10 | 2.36 | not taken |
| Experiment B* | Oxalic Acid | 4.37 | 3.68 | 2.57 | not taken | not taken | not taken |

*Not examples of the invention

As can be seen from the foregoing data, formic acid and oxalic acid were ineffective as stabilizers. In fact, the compositions employing those acids exhibited less retained DBNPA after each of the various storage intervals than did the Aqueous Control.

The acids of Examples 2–5 are observed to provide stabilizing effects of varying magnitude and duration. Specifically, salicylic acid is seen to be nearly as effective as acetic acid (see Example 1) for storage times of up to 15 days at 50° C. which corresponds to about one year of storage at room temperature (e.g., about 25° C.). Thereafter accelerated decomposition (i.e., as compared to the Aqueous Control) is observed. In addition, glycolic acid and boric acid are seen to provide relatively less initial stabilization than acetic acid and salicylic acid, however, the stabilization effect is observed to persist about twice as long as does that of salicylic acid. Citric acid is observed to exhibit initial stabilization similar to that of boric acid, however, the effect ceases after about 15 days at 50° C. (or about 1 year at about 25° C.). Thereafter acceleration of DBNPA decomposition (relative to that the Aqueous Control) is observed.

EXAMPLE 6

Aqueous P.E.G. 200 Solution of DBNPA Stabilized with Succinic Anhydride

A solution of the following composition is prepared, stored at 50° C., sampled and analyzed, all pursuant to the procedure of Example 1.

| | |
|---|---|
| DBNPA | 2.5 g |
| P.E.G. 200 | 23.5 g |
| Water | 23.5 g |
| Succinic Anhydride | 0.5 g |

After 28 days at 50° C. the composition of Example 6 has a DBNPA content of 4.16 weight percent on a total weight basis. This represents retention of about 83 percent of the DBNPA which was initially present. In contrast, after 27 days at 50° C., the corresponding non-stabilized aqueous composition (i.e., the Aqueous Control of Example 1) has a DBNPA content of only 3.5 weight percent on a total weight basis; representing retention of only 70 percent of the DBNPA which was initially present.

EXAMPLE 7

Aqueous P.E.G. 200 Solution of DBNPA Stabilized with Ethylenediaminetetraacetic Acid A solution of the following composition is prepared, stored at 50° C., sampled and analyzed, all pursuant to the procedure of Example 1.

| | |
|---|---|
| DBNPA | 2.5 g |
| P.E.G. 200 | 23.5 g |
| Water | 23.5 g |
| Ethylenediamine-tetraacetic acid (i.e., EDTA) | 0.5 g |

After 25 days at 50° C. the DBNPA content of the composition of Example 7 has described from 5.0 weight percent to 4.4 weight percent, both being on a total weight basis. In contrast, the DBNPA content of corresponding non-stabilized aqueous composition (i.e., the Aqueous Control of Example 1 above) decreases from 5 weight percent to 3.73 weight percent after only 20 days at 50° C. Thus, the presence of the EDTA is seen to provide a substantial reduction in DBNPA decomposition.

While the practice of the invention has been illustrated with reference to particular embodiments and examples, it should be understood that such embodiments and examples are not intended to limit the scope of the instantly claimed invention.

What is claimed is:

1. An aqueous antimicrobial composition having a pH from about 2 to about 5 and comprising:
    (a) an alpha-halogenated amide antimicrobial compound of the formula:

$$R_1-\underset{\underset{X}{|}}{\overset{\overset{Br}{|}}{C}}-\overset{\overset{O}{\|}}{C}-N-(R)_2$$

wherein:

X is hydrogen, halogen or a cyano radical;

each R group is independently hydrogen, a monovalent saturated hydrocarbon radical or an inertly substituted monovalent saturated hydrocarbon radical or the two R groups are jointly a divalent saturated hydrocarbon radical or an inertly substituted divalent saturated hydrocarbon radical which, taken with the adjacent nitrogen atom, forms a heterocyclic ring having from 4 to about 10 ring members; and $R_1$ is a cyano radical or an amido radical of the formula:

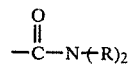

wherein R is as hereinbefore defined;
(b) a water-miscible organic solvent in an amount sufficient to dissolve the halogenated amide antimicrobial, said solvent being a normally liquid polyalkylene glycol of the ethylene, trimethylene or tetramethylene series or a mono- or di-saturated hydrocarbyl ether thereof;
(c) water; and
(d) a stabilizing amount of an acid stabilizer selected from the group consisting of acetic acid and ethylenediaminetetraacetic acid, said stabilizing amount being an amount sufficient to measurably reduce the decomposition of the halogenated amide antimicrobial in the aqueous composition.

2. The composition of claim 1 wherein the acid stabilizer is ethylenediaminetetraacetic acid.

3. The composition of claim 1 wherein the polyalkylene glycol or ether thereof has a weight average molecular weight of from about 75 to about 1000.

4. The composition of claim 1 wherein, in the antimicrobial compound:
X is hydrogen, bromine or chlorine;
each R group is independently hydrogen, a monovalent saturated hydrocarbon radical or an inertly substituted monovalent saturated hydrocarbon radical; and
$R_1$ is a cyano radical.

5. The composition of claim 2 wherein, in the antimicrobial compound:
X is hydrogen, chlorine or bromine; each R is independently hydrogen lower alkyl or phenyl; and $R_1$ is a cyano radical.

6. The composition of claim 1 wherein the antimicrobial compound is 2,2-dibromo-3-nitrilopropionamide.

7. The composition of claim 1 wherein the water-soluble organic solvent is polyethylene glycol, having a weight average molecular weight of about 200; the antimicrobial compound is 2,2-dibromo-3-nitrilopropionamide; and the pH of the aqueous antimicrobial composition is from about 3 to about 4.

8. The composition of claim 1 wherein the acid stabilizer is acetic acid.

9. The composition of claim 1 wherein:
(a) the antimicrobial compound constitutes from about 1 to about 25 weight percent of the total composition;
(b) the water constitutes from about 20 to about 60 weight percent of the total composition;
(c) the water miscible organic solvent constitutes from about 25 to about 75 weight percent of the total composition; and
(d) the acid stabilizer constitutes from about 0.1 to about 5 weight percent of the total composition.

10. A process for preparing the aqueous antimicrobial composition of claim 1 which process comprises the steps of:
(a) preparing the alpha-halogenated amide antimicrobial by the acid catalyzed reaction of the corresponding non-halogenated amide with halogen in aqueous solution, at a temperature of less than about 40° C. and in the presence of hydrogen halide at a concentration which is less than about 20 weight percent on a total weight basis but which is sufficient to catalyze the reaction;
(b) dissolving the resulting aqueous reaction mixture in the water miscible organic solvent;
(c) adding to the reaction mixture of step (a), or to the water miscible organic solvent solution of step (b), a stabilizing amount of the acid stabilizer; and
(d) adjusting the pH of the product of step (a), (b) or (c) such that the aqueous composition has a pH of from about 2 to about 5.

11. The process of claim 10 in which the pH adjustment is such that the aqueous antimicrobial composition has a pH of from about 3 to about 4.

12. The process of claim 10 wherein the halogenated amide antimicrobial is 2,2-dibromo-3-nitrilopropionamide.

13. The process of claim 10 wherein the halogenated amide antimicrobial is 2,2-dibromo-3-nitrilopropionamide; the halogen is bromine; and the water-miscible organic solvent is polyethylene glycol, or a lower alkyl ether thereof, having a weight average molecular weight of about 200.

14. The process of claim 10 wherein a water-soluble bromate is introduced to the aqueous reaction medium during preparation of the halogenated amide antimicrobial, and the pH of the aqueous reaction medium is adjusted to a value of from about 5 to about 7 by the addition of an alkali metal, or an alkaline earth metal, carbonate or bicarbonate to such reaction mixture following the preparation of the halogenated amide and prior to the dissolution of such reaction mixture in the organic solvent.

15. An aqueous antimicrobial composition having a pH of from about 2 to about 5 and comprising, based upon the total weight of such composition:
(a) from about 1 to about 25 weight percent of a halogenated amide antimicrobial of the formula:

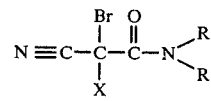

wherein X is hydrogen, chlorine or bromine and each R is independently hydrogen, an alkyl group of from 1 to about 6 carbon atoms or phenyl;
(b) from about 5 to about 90 weight percent of water;
(c) from about 5 to about 90 weight percent of a water-miscible organic solvent which is selected from the group consisting of polyethylene glycols, trimethylene glycols, tetramethylene glycols and the mono- and di-phenyl or $C_1$ to about $C_6$ alkyl ethers thereof and which has a weight average molecular weight of from about 75 to about 1000; and
(d) a stabilizing amount, in the range of from about 0.05 to about 10 weight percent, of an acid stabilizer selected from the group consisting of acetic acid and ethylenediaminetetraacetic acid.

16. The composition of claim 15 wherein the halogenated amide antimicrobial is 2,2-dibromo-3-nitrilopropionamide.

17. The composition of claim 16 wherein the water-miscible organic solvent is polyethylene glycol having a weight average molecular weight of from about 175 to about 250.

18. The composition of claim 16 wherein the water-miscible organic solvent is polyethylene glycol 200.

19. The composition of claim 17 wherein the acid stabilizer is selected from the group consisting of ethylenediaminetetraacetic acid.

20. A process for preparing the aqueous antimicrobial composition of claim 19 which process comprises the steps of:
(a) preparing the 2,2-dibromo-3-nitrilopropionamide by the reaction of cyanoacetamide with bromine in aqueous solution (1) at a temperature of less than about 40° C., (2) in the presence of HBr at a concentration which is less than about 20 weight percent on a total weight basis but which is sufficient to catalyze the reaction and (3) in the presence of an alkali metal or an alkaline earth metal bromate;
(b) dissolving the resulting aqueous reaction mixture in the polyethylene glycol having a weight average molecular weight of from about 175 to about 250;
(c) adding to the reaction mixture of step (a) or to the solution thereof of step (b) a stabilizing amount of the acid stabilizer; and
(d) adjusting the pH of the product of step (a), (b) or (c) such that the aqueous antimicrobial composition has a pH of from about 2 to about 5.

* * * * *

UNITED STATES PATENT AND TRADEMARK OFFICE
CERTIFICATE OF CORRECTION

PATENT NO. : 4,241,080

DATED : December 23, 1980

INVENTOR(S) : George A. Burk

It is certified that error appears in the above—identified patent and that said Letters Patent is hereby corrected as shown below:

Col. 3, line 61, "2bromo" should read -- 2-bromo --;

Col. 5, line 30, "glycol ether" should read -- glycol ethyl --;

Col. 5, line 66, "salts or" should read -- salts of --;

Col. 6, line 24, "cuccinic" should read -- succinic --;

Col. 9, lines 48 and 53 "DENPA" should read -- DBNPA --;

Col. 11, line 43 "that the" should read -- that of the --;

Col. 12, line 33, "described" should read -- decreased --;

Col. 12, line 34, "4.4" should read -- 4.44 --;

Signed and Sealed this

Twelfth Day of May 1981

[SEAL]

Attest:

RENE D. TEGTMEYER

Attesting Officer     Acting Commissioner of Patents and Trademarks